United States Patent [19]

Kamiyama et al.

[11] Patent Number: 5,151,102
[45] Date of Patent: Sep. 29, 1992

[54] BLOOD VESSEL COAGULATION/STANCHING DEVICE

[75] Inventors: Hiroyasu Kamiyama, 1-7-3-13 Shinkotoni, Kita-ku, Sapporo-shi; Hirokazu Amino, Kyoto, both of Japan

[73] Assignees: Kyocera Corporation, Kyoto; Hiroyasu Kamiyama, Sapporo, both of Japan

[21] Appl. No.: 530,994

[22] Filed: May 31, 1990

[30] Foreign Application Priority Data

May 31, 1989 [JP] Japan .................. 1-140192
May 30, 1990 [JP] Japan .................. 2-140376

[51] Int. Cl.$^5$ .............................................. A61B 17/39
[52] U.S. Cl. .......................................... 606/51; 606/45; 606/52
[58] Field of Search ................... 606/45, 48-52

[56] References Cited

U.S. PATENT DOCUMENTS

| | | | |
|---|---|---|---|
| 3,460,539 | 8/1969 | Anhalt, Sr. | 606/49 |
| 3,685,518 | 8/1972 | Beuerle et al. | 606/51 |
| 4,248,231 | 2/1981 | Herczog et al. | 606/48 X |
| 4,314,559 | 2/1982 | Allen | 606/49 X |
| 4,333,467 | 6/1982 | Domicone | 606/49 X |
| 4,532,924 | 8/1985 | Auth et al. | 606/50 |
| 4,765,331 | 8/1988 | Petruzzi et al. | 606/50 |

FOREIGN PATENT DOCUMENTS

| | | | |
|---|---|---|---|
| 3447156 | 7/1986 | Fed. Rep. of Germany | 606/51 |
| 3501411 | 7/1986 | Fed. Rep. of Germany | 606/51 |

*Primary Examiner*—Lee S. Cohen
*Attorney, Agent, or Firm*—Spensley Horn Jubas & Lubitz

[57] ABSTRACT

A blood vessel coagulation/stanching device for flowing high-frequency current between a pair of forceps with a blood vessel being held between the ends of the forceps to cauterize, coagulate and stanch the blood vessel, the device being characterized in that the blood vessel holding section of the forceps comprises a blood vessel contact member made of an electrically insulating sintered substance with a low thermal conductivity, and the blood vessel contact member being provided on its surface with exposed electrodes at an areal ratio between 5% and 60% to the entire surface of the blood vessel contact member. With this device, the blood vessel contact section of the forceps is not excessively heated, preventing a blood vessel from burning. This eliminates any stanching failure due to removal of a coagulated blood vessel portion and ensures superior coagulation and stanching. In addition, the exposed electrode disposed at the frontest end of the forceps has cutting, coagulation and stanching functions so that a single unit of the device can be used for coagulation, stanching and cutting.

20 Claims, 2 Drawing Sheets

BLOOD VESSEL COAGULATION/STANCHING DEVICE

BACKGROUND OF THE INVENTION

1. Field of the Invention

The present invention relates to a blood vessel coagulation/stanching device used to stop bleeding from blood vessels during cerebral nerve surgery, orthopedic surgery and general surgery operations.

2. Prior Art

A conventional bipolar-type blood vessel coagulation/stanching device uses high-frequency current. A number of such conventional devices employing a spark gap method generating high frequency ranging between 0.5 to 3 MHz have been used. The two electrodes (active and inactive electrodes) of the bipolar type device are provided at both ends of a pair of forceps to be held by hand. Electric current flows only through the living tissue held between the ends of the forceps. Since electric damage to a patient is applied only to a limited portion to be coagulated, bleeding from a blood vessel can be stopped completely without injuring other tissues. More specifically, the stanching effect of the device is obtained by coagulating the blood vessel using localized heating caused by the high-frequency current flowing through the living tissue.

However, stainless steel is mostly used as the material of the conventional forceps. Titanium which is light and corrosion resistant is also used these days. Since these forceps made of metal are high in thermal conductivity, they tend to conduct heat easily. Due to this tendency, the heat of a locally heated blood vessel is reversely transferred to the metal forceps. As the pair of forceps is used, the temperature at the front end portions of the forceps gradually rises. This causes burning between the ends of the metal forceps and the blood vessel. As a result, a part of the blood vessel attaches to the ends of the forceps. This attaching force is greater than the coagulation force of the blood vessel. When the ends of the forceps are separated from each other after the blood vessel is coagulated, the coagulation portion of the blood vessel is often separated and removed. This causes the blood vessel to tear and results in failure in stopping bleeding. In addition, the burnt substance attached to the ends (electrodes) of the forceps must be shaved off and cleaned for the subsequent use. This shaving and grinding work causes inexpedient problems: change in the shapes of the ends of the forceps and the reduction in the accuracy of the forceps.

SUMMARY OF THE INVENTION

To solve the above-mentioned problems, the inventors of the present invention have conducted a variety of examinations and experiments. The inventors succeeded in improving the device by using an electrically insulating sintered substance, such as zirconia ceramics, with a low thermal conductivity as the most effective means to prevent living tissues from burning and attaching to the ends of the forceps, and also by fabricating exposed electrodes made of conductive resin adhesive from the insulating sintered substance to prevent temperature from rising and heat from transferring from a blood vessel to the ends of the forceps, completely stopping bleeding. The inventors thus provide the invention as detailed below.

DETAILED DESCRIPTION OF THE INVENTION

Figure 1:
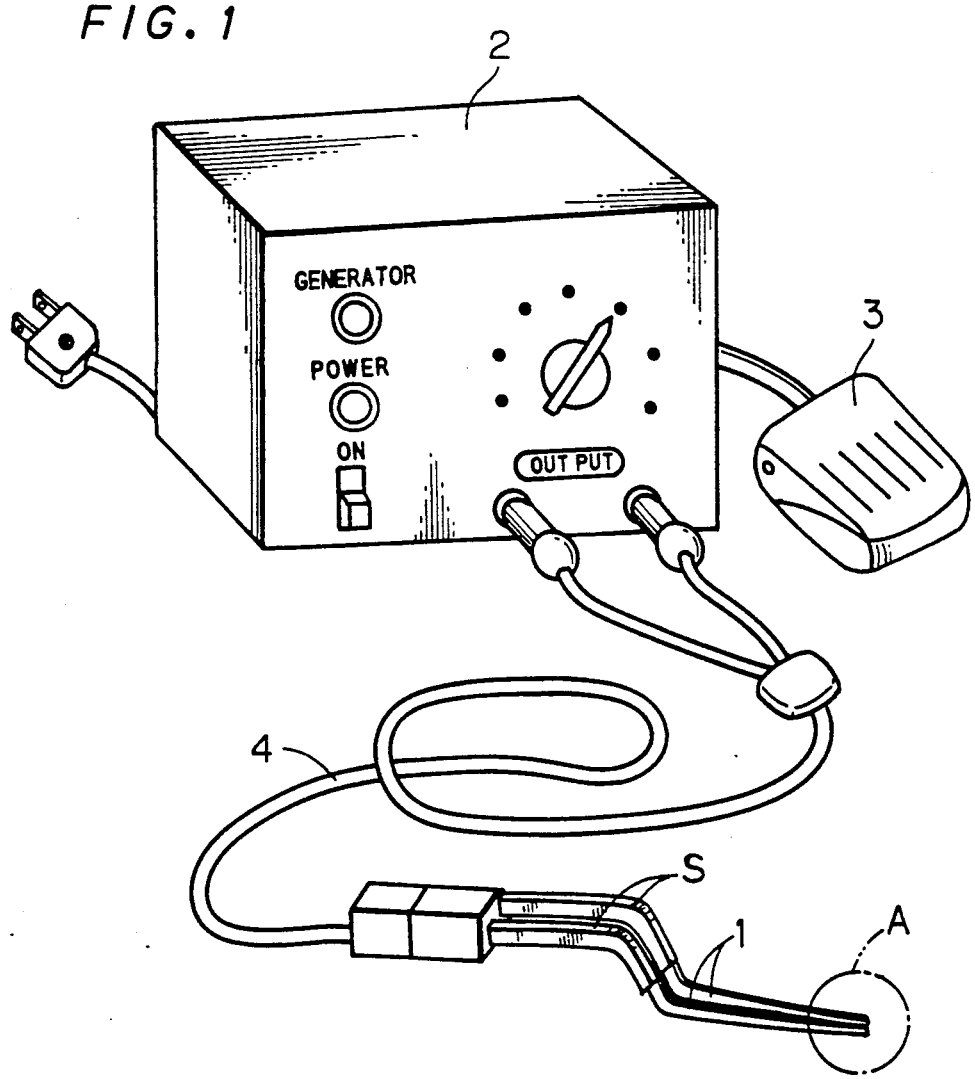
FIG. 1 illustrates an overall structure of the blood vessel coagulation/stanching device of the present invention.
Figure 2:
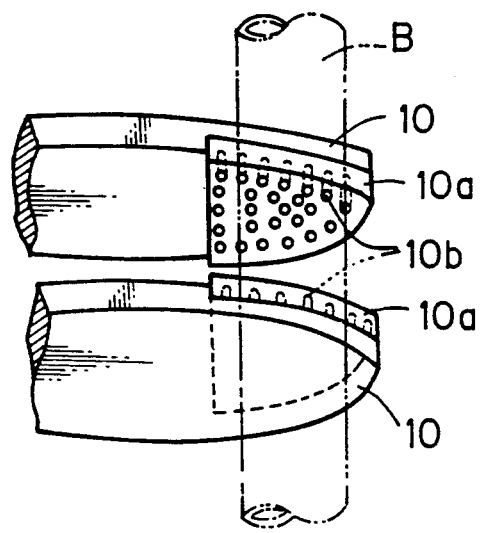
FIG. 2 is a partially enlarged perspective view of section A of FIG. 1.
Figure 3:
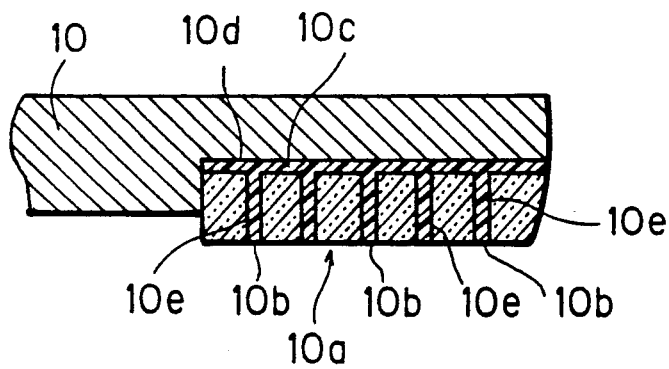
FIG. 3 is an enlarged vertical sectional side view of the end of the forceps including the blood vessel contact member shown in FIG. 2.

Embodiments of the present invention are explained below referring to the attached drawings. FIG. 1 illustrates an overall structure of the bipolar-type blood vessel coagulation/stanching device of the present invention. Numeral 1 represents a pair of forceps used to hold and coagulate a blood vessel to stop bleeding. The grip sections of the forceps 1 are covered with insulation coating S. Ends A of the forceps 1, enlargedly shown in FIG. 2, are comprised of a pair of blood vessel holding sections 10 made of stainless steel or titanium. The inside surface of the blood vessel holding section 10, which actually contacts blood vessel B, is comprised of a blood vessel contact member 10a made of an electrically insulating sintered substance. On the blood vessel contact member 10a, exposed electrodes 10b composed of conductive resin adhesive are provided. Numeral 2 represents a power source unit used to generate high-frequency current. The power of the power source unit 2 to be supplied to the forceps 1 via a cord 4 is turned on and off by a foot switch 3. The inventors used conductive resin "DOTITE" (trade name) made by Fujikura Chemical Co., Ltd. as conductive resin adhesive. This conductive resin adhesive includes high purity silver powder as conductive filler and highly heat resistant epoxy resin. The adhesive is a non-solvent, single-solution type with 100% solid content. The properties of the adhesive are listed in Table 1.

TABLE 1

| Contents | Silver powder, epoxy resin, curing agent |
|---|---|
| Appearance | Silver white paste |
| Viscosity | 300 to 500 poise (Viscotester VT-02) |
| Specific gravity | 2.7 (specific gravity cup method) |
| Specific resistance | $5.0 \times 10^{-4}$ Ω-cm or less |
| Adhesion strength | 75 kg/cm$^2$ (tensile/shearing strength of JIS K6850, Cu-Cu) |

The blood vessel contact member 10a is made of an electrically insulating sintered substance (ceramics) such as zirconia. The sintered substance is highly corrosion resistant and very hard. The thermal conductivity of a zirconia sintered substance for example is 0.009 cal·cm/cm$^2$·sec·°C. at 20° C. This value is far smaller than 0.039 cal·cm/cm$^2$·sec·°C. of stainless steel and 0.04 cal·cm/cm$^2$·sec·°C. of titanium. The thermal conductivity of the ziroconia sintered substance is thus smaller than those of such metal materials. Therefore, the heat generated by the flow of the high-frequency current from the exposed electrodes 10b to a blood vessel is far less radiated through the blood vessel contact members 10a made of the sintered substance. This prevents a part of a cauterized blood vessel from attaching to the blood vessel contact members 10a.

In the preferred embodiment of the present invention, the exposed electrodes 10b are dispersed like multi dots on the blood vessel contact members 10a and made of conductive resin adhesive. More particularly, a plurality of small through holes 10e are provided on the insulating blood vessel contact members 10a made of a sintered substance such as zirconia. In the through holes 10e, the above-mentioned conductive resin adhesive is filled in order to secure the contact member 10a of a flat chip shape in a recess 10d formed at the front end portion of the blood holding section 10 via a conductive resin adhesive layer 10c. In addition, the conductive resin adhesive is exposed from the through holes 10e on the front surface side to disperse the exposed electrodes 10b like multi dots. The proper areal ratio of the electrodes 10b disposed over the surface of the blood contact member 10a ranges between 5% and 60%. If the ratio exceeds 60%, the mechanical strength of the blood contact member 10a made of ceramics becomes small; if the ratio is less than 5%, no proper cauterization and stanching effect can be obtained as confirmed by the inventors' experiments. Since the exposed electrodes 10b of this embodiment are dispersed like multi dots as described above, electric current from the blood vessel contact member 10a to blood vessel B is almost uniform, preventing excessively localized heating. The blood vessel contact members 10a can also be secured to the blood vessel holding sections 10 by using the exposed electrodes 10b made of the conductive resin adhesive. This can greatly increase production efficiency.

The surfaces of the blood vessel contact members 10a must be ground like a mirror surface with a surface roughness of 1Ra or better so that substances burnt and attached to the surfaces of the members 10a can be easily removed.

The Vickers hardness of the zirconia ceramics is 1250 kg/mm$^2$ or more, far harder than those of metal materials such as stainless steel and titanium.

Therefore, even when a partial tissue of a blood vessel is burnt and firmly attached to the blood vessel contact members 10a made of the sintered substance, such a tissue can be easily shaved off with a knife without damaging the surfaces of the contact members.

Figure 4:
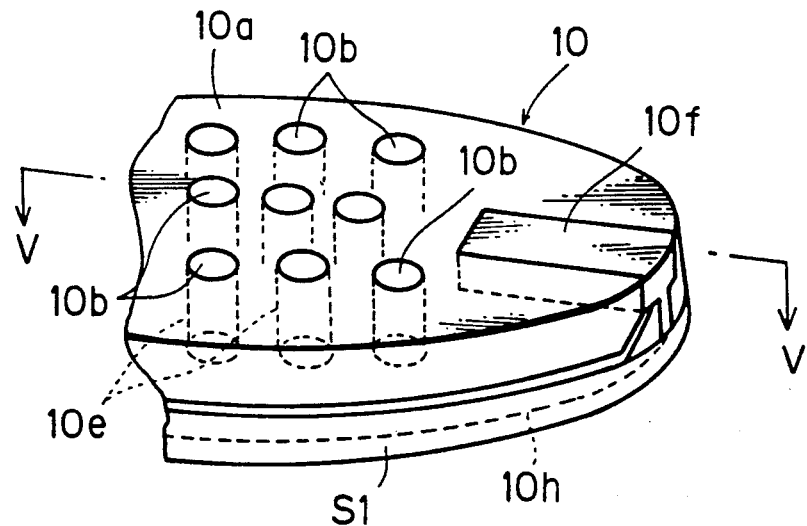
FIG. 4 is a partially enlarged perspective view of the end of the forceps of a developed embodiment of the present invention.
Figure 5:
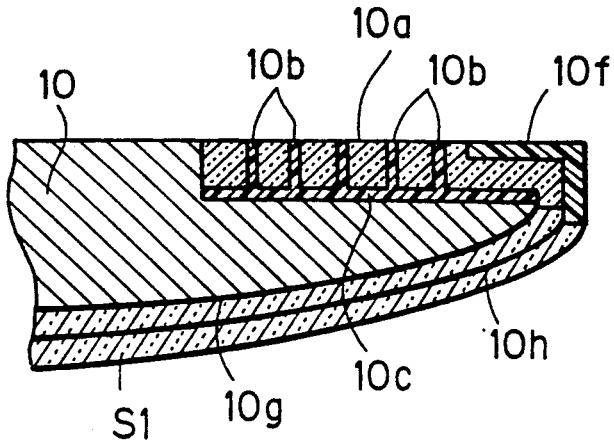
FIG. 5 is a sectional view taken on line V—V of FIG. 4.

A developed embodiment of the present invention is then explained below referring to FIGS. 4 and 5. This developed embodiment further comprises an exposed electrode 10f disposed at the front end of the blood vessel contact member 10a. In addition to coagulation and stanching, cutting of blood vessels is possible with the exposed electrode 10f. This feature is offered to meet the following needs. During operation, many blood vessels must be stanched and cut at their centers to advance to a deeper section. At this time, it is necessary to transfer tools from the forceps to scissors to cut the stanched section of each blood vessel when a device without cutting function is used, so that the operator must frequently transfer tools from forceps to scissors and from scissors to forceps. This transfer is extremely troublesome and makes operation time longer.

When the cutting function is incorporated by using the electrode capable of coagulating, stanching and cutting blood vessels, the operator can continue stanching and cutting while holding the forceps. This eliminates the need for tool transfer when removing burnt tissues to clean the forceps and when cutting blood vessels. As a result, operation time can be significantly shortened.

To accomplish the above-mentioned purposes, the exposed electrode 10f disposed at the frontest end of the forceps is formed in a shape of an oblong rectangular plate and has an area wider than those of other exposed electrodes 10b. A power supply wire 10h connected to the electrode 10f differs from a power supply wire 10g connected to the exposed electrodes 10b. The power supply wire 10h is embedded in an insulation coating S1. Switching between the power supply wires 10g and 10h is controlled by the foot switch 3 for example. For coagulation and stanching work, high-frequency current with a mild rising waveform is applied to both exposed electrodes 10b and 10f. For cutting a blood vessel, the exposed electrodes 10b are turned off and pulse current with a steep rising waveform is applied only to the exposed electrode 10f. It is desirable that both the exposed electrode 10f and the exposed electrodes 10b are formed by using conductive resin adhesive having the properties already listed in Table 1.

Unlike the conventional device, this developed embodiment eliminates the need for tool transfer from forceps to scissors when cutting a blood vessel using the exposed electrode 10f after coagulation and stanching. Coagulation, stanching and cutting can be done by a single pair of forceps, ensuring higher convenience.

In addition to the preferred and developed embodiments described above, the present invention can have the following selectable embodiments.

a) Instead of metal, plastics or ceramics can be used as the material of the forceps, provided inside the forceps, conductive wires or patterns are embedded to provide electric conductivity.

b) The blood vessel contact member is extended beyond the blood contact section and formed over the entire surface of the forceps to facilitate moulding.

c) Instead of applying pulse current with a steep rising waveform to the exposed electrode for cutting, high-frequency current with high current energy is applied for cutting.

The above-mentioned bipolar-type blood vessel coagulation/stanching device with the forceps of the present invention can offer the effects described below.

(1) Stanching is ensured during operation. This significantly shortens operation time.

(2) The amount of bleeding can be reduced. This lightens operating damage to a patient.

(3) Labor for shaving off a substance attached to the ends of the forceps can be saved. Even if such a substance is attached to the ends, it can be scraped off easily. Since the ends of the forceps are very hard, their shapes can remain unchanged. This ensures the high accuracy of the forceps for an extended period of time.

(4) By using the conductive resin adhesive as the electrodes, the electrodes can be formed easily in complicated shapes, greatly improving production efficiency.

(5) The thermal stress generated due to the difference in the thermal expansion coefficient between metal and ceramics can be absorbed by the conductive resin adhesive including metal powder at the adhesive layer during autoclave sterilizing. The ceramics of the blood vessel contact member can thus be prevented from breaking and can have a longer service life. Autoclave sterilizing is thus possible, eliminating the need for use of gas sterilizing. This greatly reduces sterilizing time.

(6) In the case of the developed embodiment, a single pair of forceps can be used to coagulate, stanch and cut blood vessels. This eliminates the need for use of scissors and for transfer of tools, ensuring easy operation. This benefit is highly evaluated, particularly in a case of operation extending for a long time, because a lot of troublesome work can be saved and operation time can be shortened,

We claim:

1. In a bipolar-type blood vessel coagulation/stanching device having a pair of conductive forceps including blood vessel holding sections provided at end portions of said forceps and adapted to cauterize, coagulate and stanch said blood vessel, the improvement comprising:

an electrically and thermally insulative blood vessel contact member of sintered substance provided at each of said end portions, each of said contact members having a blood vessel contact surface which includes a plurality of exposed electrodes at an areal ratio between 5% and 60% to the entire surface area of said blood vessel contact surface of said blood vessel contact member.

2. A blood vessel coagulation/stanching device according to claim 1, wherein said exposed electrodes are made of conductive resin adhesive.

3. A blood vessel coagulating/stanching device according to claim 2, wherein each said blood vessel contact member defines a plurality of through holes and said electrodes comprise said conductive resin adhesive filled in said through holes, said electrodes being exposed at said blood vessel contact surface, said exposed electrodes being dispersed over the blood vessel contact surface of said blood vessel contact member.

4. A blood vessel coagulating/stanching device according to claim 3, wherein a contact member further comprises a cutting electrode provided at a front most end of said blood vessel contact member.

5. A blood vessel coagulating/stanching device according to claim 2, wherein said conductive resin adhesive is an epoxy resin-based, non-solvent, single-solution type conductive resin adhesive with 100% solid content, including high purity silver powder.

6. A blood vessel coagulating/stanching device according to claim 1, wherein each forcep end portion defines a recess and each blood vessel contact member has a flat chip shape and is received in an associated recess of said forceps, said device further comprising a conductive resin adhesive layer between each blood vessel contact member and the associated end portion of said forceps.

7. A blood vessel coagulation/stanching device according to claim 1, wherein said blood vessel contact member is extensively provided over the entire surface of said forceps.

8. A blood vessel coagulating/stanching device according to claim 1, wherein said sintered substance is ceramics made of one of zirconia, alumina, silicon nitride and silicon carbide.

9. A device for passing current through living tissue to coagulate the tissue, comprising:

a pair of elongated members, said elongated members being adapted to be brought into physical proximity to each other at a distal end of each elongated member, each elongated member having an electrically insulative and thermally insulative tissue contact member provided at its associated distal end, each tissue contact member having a tissue contact surface opposing the tissue contact surface of the other tissue contact member, each tissue contact surface having a plurality of electrodes, each electrode having a predetermined size and spacing from the other electrodes of the tissue contact surface so as to inhibit overheating of the tissue contact surface by the coagulated tissue; and coupling means for insulatively coupling said members at proximal ends thereof.

10. The device according to claim 9 wherein said tissue contact member defines at least one through hole, at least one of said electrodes being received in said through hole.

11. The device according to claim 10 wherein said tissue contact member defines a plurality of through holes substantially uniformly dispersed over the tissue contact surface, a corresponding number of said electrodes being received in said through holes.

12. The device according to claim 11 wherein said electrodes cover an area of between 5% and 60% of the entire tissue contact surface of said tissue contact member.

13. The device according to claim 10 wherein said electrode comprises a conductive resin adhesive filled in said through hole.

14. The device according to claim 13 wherein said conductive resin adhesive comprises an epoxy resin-based, non-solvent, single-solution type adhesive with 100% solid content, containing high purity silver powder therein.

15. The device according to claim 9 further comprising a conductive resin adhesive layer provided between said electrically non-conductive tissue contact member and each of said elongated members.

16. The device according to claim 9 further comprising a cutting electrode provided at a front most end of said tissue contact member, said cutting electrode being electrically insulated from said electrodes.

17. The device according to claim 9 wherein said electrically non-conductive tissue contact member comprises a ceramic.

18. A device according to claim 17 wherein said ceramic comprises any one of zirconia, alumina, silicon nitride and silicon carbide.

19. A blood vessel coagulation/stanching device comprising:

a pair of electrically conductive elongated members;

coupling means for insulatively coupling said members at proximal ends thereof;

an electrically and thermally insulative ceramic tissue contact member provided adjacent a distal end of each of the elongated members, each of said tissue contact members further having a polished tissue contact surface and defining a plurality of through holes substantially uniformly dispersed over said tissue contact polished surface of said tissue contact member at an areal ratio between 5% and 60% to the entire area of said tissue contact surface of said tissue contact member;

a plurality of electrodes of conductive resin adhesive received in said through holes and being exposed at said tissue contact surface of each of said tissue contact members; and a conductive resin adhesive layer provided between each non-conductive tissue contact member and the associated conductive elongated member thereby electrically coupling said electrodes and the associated conductive elongated member.

20. The blood vessel coagulation/stanching device according to claim 19 further comprising a cutting electrode provided adjacent a front most end of one of said tissue contact members.

* * * * *